US008695810B2

(12) United States Patent
Gao

(10) Patent No.: US 8,695,810 B2
(45) Date of Patent: Apr. 15, 2014

(54) SUPEROLEOPHOBIC AND SUPERHYDROPHILIC FABRIC FILTERS FOR RAPID WATER-OIL SEPARATION

(75) Inventor: Di Gao, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 334 days.

(21) Appl. No.: 13/157,879

(22) Filed: Jun. 10, 2011

(65) Prior Publication Data

US 2011/0303620 A1 Dec. 15, 2011

Related U.S. Application Data

(60) Provisional application No. 61/353,487, filed on Jun. 10, 2010.

(51) Int. Cl.
*B01D 24/00* (2006.01)
*B01D 39/00* (2006.01)
*B01D 37/00* (2006.01)
*B01D 67/00* (2006.01)

(52) U.S. Cl.
USPC ........ 210/500.1; 210/503; 210/504; 210/767; 264/48

(58) Field of Classification Search
USPC .......... 210/500.1, 508, 767, 799, 242.4, 503, 210/504; 516/199; 106/287.25; 514/772; 424/78.08; 252/79.1; 264/48
See application file for complete search history.

(56) References Cited

U.S. PATENT DOCUMENTS

| 2,804,391 | A | * | 8/1957 | Doan et al. ................. | 106/18.34 |
| 3,112,241 | A | * | 11/1963 | MacKenzie ................ | 162/164.6 |
| 3,142,612 | A | * | 7/1964 | Reiman ........................ | 162/145 |
| 3,812,217 | A | * | 5/1974 | Moyer ......................... | 558/152 |
| 3,962,798 | A | * | 6/1976 | Jackson ......................... | 34/340 |
| 3,976,572 | A | * | 8/1976 | Reick ............................. | 210/94 |
| 4,372,847 | A | * | 2/1983 | Lewis ............................ | 210/86 |
| 4,394,126 | A | * | 7/1983 | Wilson ......................... | 8/115.6 |
| 4,707,269 | A | * | 11/1987 | Ohue et al. ..................... | 210/651 |
| 4,717,744 | A | * | 1/1988 | Boutevin et al. ............... | 524/17 |
| 4,784,788 | A | * | 11/1988 | Lancz ........................... | 510/396 |
| 5,102,724 | A | * | 4/1992 | Okawahara et al. .......... | 442/199 |
| 5,344,930 | A | * | 9/1994 | Riess et al. ..................... | 544/84 |
| 5,531,890 | A | * | 7/1996 | Keenan ....................... | 210/242.4 |
| 7,736,696 | B2 | * | 6/2010 | Piana et al. .................... | 427/240 |
| 8,513,342 | B2 | * | 8/2013 | Gao et al. ..................... | 524/267 |
| 2004/0178150 | A1 | * | 9/2004 | Denton et al. ................ | 210/691 |
| 2006/0006109 | A1 | * | 1/2006 | Klein et al. ................... | 210/299 |
| 2009/0032475 | A1 | * | 2/2009 | Ferrer et al. ................... | 210/799 |
| 2009/0038510 | A1 | * | 2/2009 | Acosta et al. ............. | 106/287.25 |
| 2009/0286885 | A1 | * | 11/2009 | Qiu et al. ...................... | 514/772 |
| 2011/0091408 | A1 | * | 4/2011 | Raghavanpillai .......... | 424/78.08 |
| 2011/0092410 | A1 | * | 4/2011 | Raghavanpillai ............ | 510/528 |
| 2011/0303620 | A1 | * | 12/2011 | Gao ............................ | 210/776 |

(Continued)

OTHER PUBLICATIONS

Buck et al., Chemistry, Properties, and Uses of Commercial Fluorinated Surfactantnts, 2012.*

*Primary Examiner* — Ana Fortuna
(74) *Attorney, Agent, or Firm* — David G. Oberdick; Peter J. Borghetti

(57) ABSTRACT

Product, method of making product, and technique for using product to separate oil from water via a filter, such as cotton, polyester, or leather, coated with a chemical that blocks oil while allowing water to pass therethrough.

4 Claims, 2 Drawing Sheets

(56) References Cited

U.S. PATENT DOCUMENTS

| | | | |
|---|---|---|---|
| 2012/0073907 A1* | 3/2012 | Seemeyer et al. | 184/15.3 |
| 2012/0121877 A1* | 5/2012 | Levchik et al. | 428/220 |
| 2013/0102685 A1* | 4/2013 | Calvarese et al. | 514/772 |

* cited by examiner

SUPEROLEOPHOBIC AND SUPERHYDROPHILIC FABRIC FILTERS FOR RAPID WATER-OIL SEPARATION

CROSS-REFERENCE TO RELATED APPLICATIONS

This application is a Non-provisional Application of U.S. Provisional Application No. 61/353,487, titled: SUPEROLEOPHOBIC AND SUPERHYDROPHILIC FABRIC FILTERS FOR RAPID WATER-OIL SEPARATION, filed on Jun. 10, 2010, herein incorporated by reference.

FIELD OF THE INVENTION

The present invention is related generally to the field of contamination separation, and in particular the separation of oil from sea water.

BACKGROUND OF THE INVENTION

A technique for separating oil from water via a cotton, polyester, or leather filter coated with a chemical that blocks the contaminant, such as oil, while allowing water to pass through does not exist that removes 95% or more of the contaminant from the water.

SUMMARY OF THE INVENTION

According to the invention, there is provided a Superoleophobic and Superhydrophilic Fabric Filter, as defined in claims 1-13.

The present invention is an article and a technique for separating oil from water via, for example, a cotton, polyester, or leather filter coated with a chemical that blocks oil while allowing water to pass through.

For a better understanding of the present invention, together with other and further embodiments thereof, reference is made to the accompanying drawings and detailed description.

BRIEF DESCRIPTION OF THE DRAWINGS

The present invention is illustratively shown and described in reference to the accompanying drawings, in which.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein.

Figure 1A:
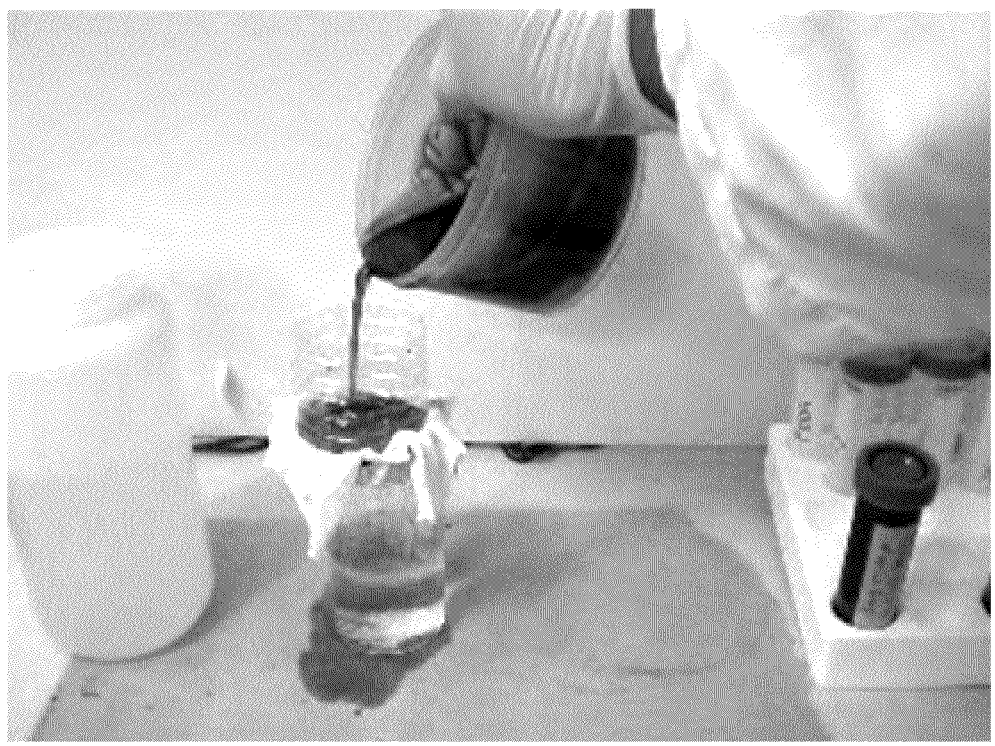
FIGS. 1a-1b are pictorial images of the present invention demonstrating separation of sea water from crude oil using a treated cotton filter, and illustrating on the surface of treated cotton, water (stained with a blue dye to aid the observation) easily spreads, while oil forms a bead.
Figure 1B:
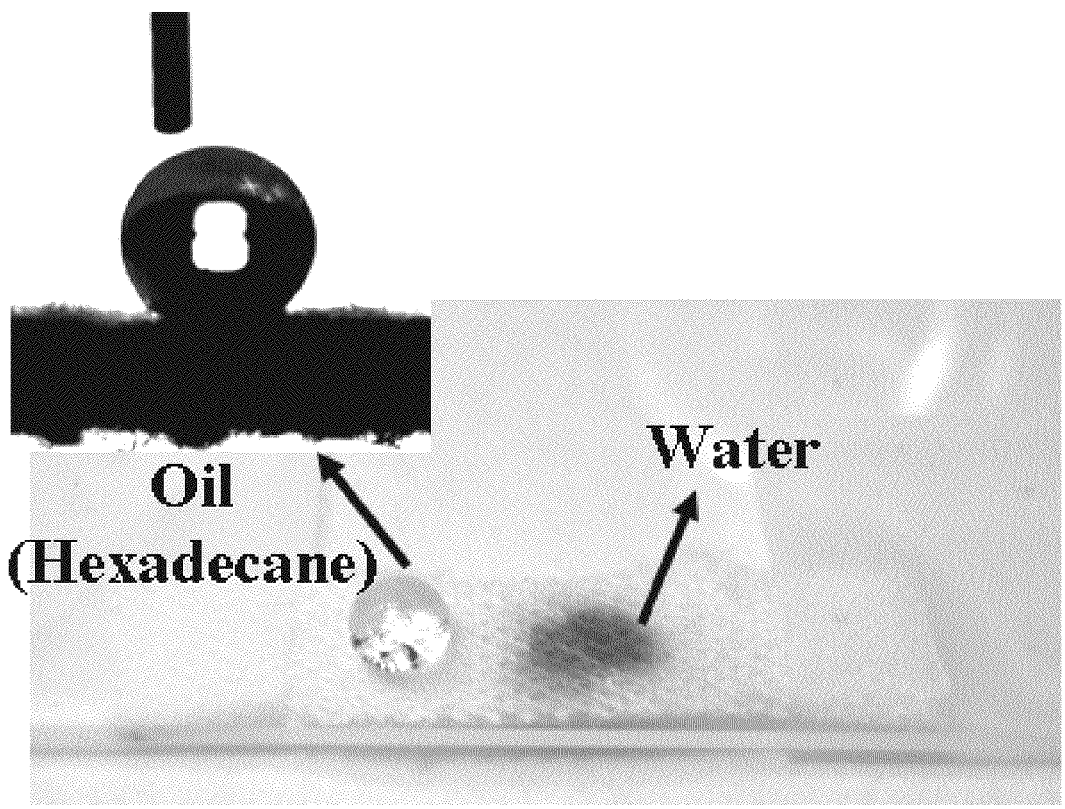

Now turning to FIG. 1a that illustrates one embodiment of the present invention filtering oil from contaminated water samples. The filter includes a chemical that is both hydrophilic and oleophobic. On the surface of ordinary cotton treated with the chemical, water easily spreads, while oil forms beads, as shown in FIG. 1b. When used as a filter, such treated fabric of cotton, polyester, or leather allows water to pass through it but does not allow oil to pass through it. The filter can be produced by submerging the cotton in an aqueous solution containing the chemical then drying it in an oven or in open air. The size of the fabric can be tailored to the size of the devices that remove contamination in a body of water. For example, the massive slick off the Gulf Coast may require large, trough-shaped filters that could be dragged through the water to capture surface oil. The oil could be recovered and stored and the filter reused.

The cost for treating the fabric with the chemical of the present invention is very low, estimated to be less than $0.1 per square foot of fabric. Only very small amount of chemical is needed to treat the cotton or equivalent fabric. It is estimated that 1 pound of the chemical is enough to treat more than 2,000 square foot cotton or fabric.

The chemical binds strongly to the cotton. Experiments have demonstrated that the treated fabric being submerged in water-oil mixture for more than a month without noticing significant change in either the oil-repellency of the cotton or the separation efficiency of the filter.

One embodiment of the chemical composition comprises at least one oleophobic section (typically fluorocarbon groups) and one hydrophilic section (typically groups that possess positive or negative charges in an aqueous solution). Such chemicals may be selected from a large pool of candidates. The chemicals can be either synthesized or commercially available. The three methods that are described below are examples for preparing such chemicals and not meant to limit the invention Methods for Producing the Fluorinated Chemical Method 1 (Products are Mono Phosphate Ester and Small Amount of Bis Phosphate Ester)

The fluoroalkyl phosphates were synthesized according to Scheme 1 (below). Briefly, 3,3,3-trifluoro-1-propanol is added to equal molar phosphoryl chloride with vigorous stirring at such a rate that the temperature is kept between about 20° C. and about 30° C., but most preferably about 25° C. The resulting mixture is warmed to about 45° C. to 55° C., but most preferably about 50° C. for about 4 hours 30 minutes to 5 hours 30 min, but most preferably about 5 hr, and the evolving hydrogen chloride is removed from the reaction mixture by reducing the pressure to 0.5-1 atm. After cooling to room temperature, the final mixture is poured into a water/ice mixture and stirring is continued for about 4 hours 30 minutes to 5 hours 30 min, but most preferably about 5 hours. Then, ether is added, and the organic layer is separated by density difference. Evaporation of the ether yields the product containing fluoroalkyl phosphates. Diethanolamine (DEA) salts of the fluoroalkyl phosphates are prepared by neutralizing the phosphates with appropriate amounts of diethanolamine by stoichiometry.

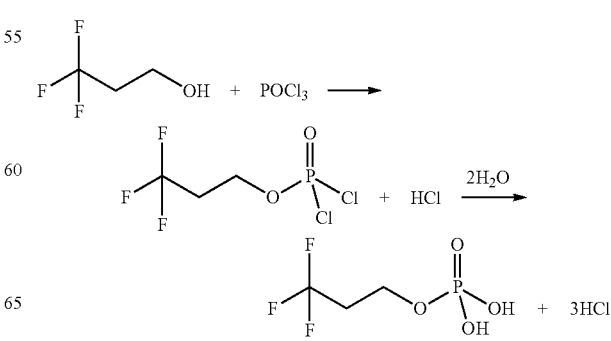

-continued

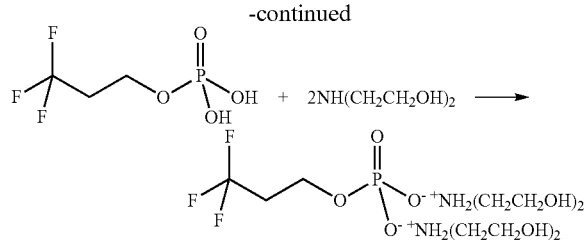

Method 2 (the Products are Mixture of Mono Phosphate Ester and Bis Phosphate Ester)

In one embodiment of the present invention, 142 g±14 g (1.0 mole±0.1 mole) of phosphorus pentoxide is gradually added to 342.21 g+34 g (3±0.3 moles) of 3,3,3-trifluoro-1-propanol in a 1000 ml three-necked flask with stirring at such a rate that the temperature is kept, by cooling, about 50° C.±5° C. The mixture is left to react for about 3 hours 30 minutes to 4 hours 30 minutes at about 75° C. to about 85° C., but most preferrably about 80° C. After addition of 54 g±5 g DI water, the mixture is stirred for another about 2 hours 30 minutes to 3 hours 30 min, but most preferrably 3 hours at about 75° C. to about 85° C., but most preferrably about 80° C. Thereafter, appropriate amounts of diethanolamine were added for neutralization by stoichiometry. The product is obtained by extraction with ethyl ether and distillation.

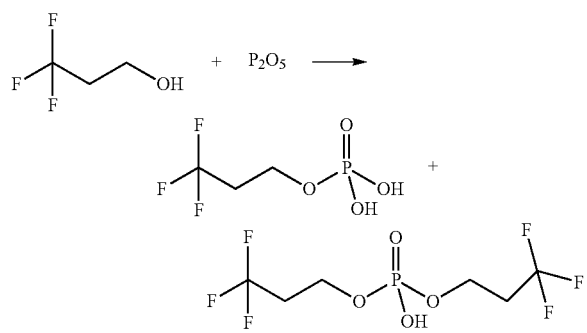

Method 3

In one embodiment of the present invention, 100 g±10 g (0.67 mole±0.07 mole) methydichorophosphate (MePOCl$_2$) is added drop-wise to a mixture of 300 mL±30 mL anhydrous ether, 131.93 g±13 g (1.67 mole±0.17 mole) pyridine, and 1.67 mole±0.17 mole 3,3,3-trifluoro-1-propanol under stirring at approximately about 3° C. to 7° C., but most preferrably 5° C. The mixture is refluxed for about 1 hour 30 minutes to 2 hours 30 min, but most preferrably about 2 hours. The reaction mixture is cooled in a refrigerator and pyridinium salt is then filtered. The filtrate is washed first by 10 w.t. % sulfuric acid solution in NaCl saturated distilled water and then by NaCl saturated distilled water alone. The resultant organic phase is dried over MgSO$_4$ and then fractionated 3 times. Final distillates of the products are collected.

The technology for treating a fabric with Superoleophobic and Superhydrophilic chemicals to form fabric filters may also find use in many other applications where water needs to be separated from oil, including separating gross amounts of oil from the wastewater effluents of oil refineries, petrochemical plants, chemical plants, natural gas processing plants and other industrial sources, and separating oil from the bilge water accumulated in ships as required by the international MARPOL Convention.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A superoleophobic and superhydrophilic fabric filter for rapid water-oil separation comprising:
    a chemical composition having hydrophilic and oleophobic properties, wherein the chemical composition is

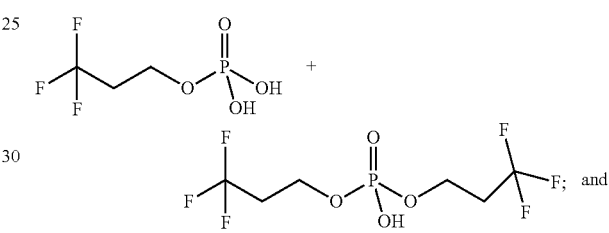

a fabric treated with the chemical,
        wherein 95% or more of the oil contaminate is separated from the water.
2. The fabric filter according to claim 1, wherein the fabric is cotton, polyester, or leather.
3. A superoleophobic and superhydrophilic fabric filter for rapid water-oil separation comprising:
    a chemical composition having hydrophilic and oleophobic properties, wherein the chemical composition is

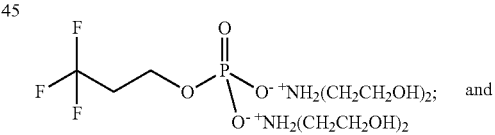

a fabric treated with the chemical,
        wherein 95% or more of the oil contaminate is separated from the water.
4. The fabric filter according to claim 3, wherein the fabric is cotton, polyester, or leather.

* * * * *